United States Patent [19]

Petronella

[11] 4,337,208

[45] Jun. 29, 1982

[54] PROCESS FOR THE PRODUCTION OF OIL-SOLUBLE METAL SALTS

[75] Inventor: Joseph Petronella, Old Bridge Township, Middlesex County, N.J.

[73] Assignee: Tenneco Chemicals, Inc., Piscataway, N.J.

[21] Appl. No.: 234,514

[22] Filed: Feb. 17, 1981

[51] Int. Cl.$^3$ .......................... C07F 15/02; C11C 1/00
[52] U.S. Cl. .................... 260/414; 260/429 R; 260/429.3; 260/429.5; 260/429.7; 260/429.9; 260/435 R; 260/438.5 R; 260/439 R; 260/446; 260/447; 260/448 R
[58] Field of Search ................ 260/413 S, 414, 439 R, 260/429 R, 429.3, 429.5, 429.7, 429.9, 435, 438.5 R, 446, 447–448 R

[56] References Cited

U.S. PATENT DOCUMENTS

| | | | |
|---|---|---|---|
| 2,650,932 | 9/1953 | Kebrich | 260/413 |
| 2,753,364 | 7/1956 | Boner et al. | 260/413 |
| 3,476,786 | 11/1969 | Lally et al. | 260/413 |
| 4,218,385 | 8/1980 | Pike | 260/414 |

*Primary Examiner*—John F. Niebling
*Attorney, Agent, or Firm*—Evelyn Berlow

[57] ABSTRACT

Oil-soluble metal salts are produced by the reaction of a polyvalent metal, such as nickel, with an organic monocarboxylic acid in the presence of an ammonium salt catalyst, water, oxygen, and an inert, water-immiscible organic solvent.

10 Claims, No Drawings

PROCESS FOR THE PRODUCTION OF OIL-SOLUBLE METAL SALTS

This invention relates to a process for the production of oil-soluble metal salts. More particularly, it relates to a process for the production of metal salts by direct metal reaction using an ammonium salt catalyst.

Oil-soluble metal salts are widely used as paint, varnish, and printing ink driers, as lubricant additives, as oxidation catalysts for the chemical industry, and as fuel oil additives. These metal salts are produced either by double decomposition processes employing a water-soluble salt of the metal and an alkali metal salt of an organic monocarboxylic acid, by the fusion of an organic monocarboxylic acid with the oxide, hydroxide, carbonate, acetate, or other suitable compound of the metal, or by the direct reaction of the metal with an organic monocarboxylic acid.

The double decomposition processes and the fusion processes have disadvantages that limit their use in the commercial production of oil-soluble metal salts of organic acids. The double decomposition processes require the use of relatively costly water-soluble metal salts and complicated processing equipment, and they yield products that are contaminated with reaction by-products that must be removed before the metal salts can be used in most applications. The fusion processes, which are more direct and less costly to carry out than the double decomposition processes, cannot be practiced with all of the polyvalent metals. In addition, some of these processes are not economical because the cost of the metal content of the metal compounds that are used in them is higher than that of the metal itself. The processes involving the direct metal reaction for the production of oil-soluble metal salts that have been disclosed in the prior art usually call for heating a metal with an organic monocarboxylic acid in the presence of water and oxygen. When carried out in the presence of a catalyst, such as a lower aliphatic acid, sulfuric acid, and/or a metal halide, these processes, when used to produce oil-soluble salts of nickel, cobalt, and other corrosion-resistant metals, require very long reaction periods and/or the use of large amounts of water and/or glycols or glycol ethers to produce commercially-useful products.

This invention relates to an improved process for the production of oil-soluble metal salts by the direct reaction of a polyvalent metal with an organic monocarboxylic acid. It makes possible the efficient production of oil-soluble salts of nickel, cobalt, and other corrosion-resistant metals that cannot be prepared by the previously-known direct metal reaction processes and it substantially reduces reaction time of those that can be produced by these processes. This process gives excellent yields of metal salts in reaction times that are considerably shorter than those of the direct metal reaction processes of the prior art. Unlike the commercially-available metal salt compositions that may contain as much as 25% of free organic acid, nickel salt solutions and other metal salt solutions prepared by the process of this invention contain little or no free acid.

In accordance with this invention, it has been found that oil-soluble salts of polyvalent metals can be prepared rapidly and efficiently by heating a polyvalent metal with an organic monocarboxylic acid in the presence of an ammonium salt catalyst, water, oxygen, and an inert water-immiscible organic solvent until substantially all of the metal has reacted.

While this process is of particular value in the preparation of salts of metals that are very resistant to corrosion, such as nickel and cobalt, that cannot be prepared efficiently by the previously-known direct metal reaction processes, it can also be used to produce oil-soluble salts of polyvalent metals that are ordinarily classified as corrosion resistant, for example, aluminum, strontium, zinc, iron, cadmium, zirconium, bismuth, chromium, lead, manganese, antimony, tin, and molybdenum, as well as those that are less resistant to reaction with organic acids. A single polyvalent metal or a combination of two or more of these metals may be used in the process of this invention.

The metal is usually used in the form of powder, granules, wire, shavings, or the like so that a large metal surface is exposed to the acid and the conversion of the metal to its salt is readily accomplished.

A wide variety of organic monocarboxylic acids can be used in the process of this invention. They include aliphatic acids, cycloaliphatic acids, aromatic acids, and mixtures of these acids. The preferred monocarboxylic acids are saturated and unsaturated aliphatic and cycloaliphatic monocarboxylic acids having from 5 to 18 carbon atoms. Examples of these preferred acids include n-pentanoic acid, 2-methylbutanoic acid, n-hexanoic acid, 2-ethylbutanoic acid, n-heptanoic acid, n-octanoic acid, 2-ethylhexanoic acid, 2-ethyl-4-methylpentanoic acid, n-nonanoic acid, neononanoic acids, isononanoic acids, 2-methylnonanoic acid, 2-ethyloctanoic acid, n-decanoic acid, neodecanoic acid, dodecanoic acid, tetradecanoic acid, octadecanoic acid, 2-ethyl-3-propylacrylic acid, octenoic acid, 10-undecenoic acid, oleic acid, naphthenic acids, rosin acids, and terpene acids. A single monocarboxylic acid or a mixture of these acids can be used in the process of this invention. Commercially-available mixtures of acids that can be used include tall oil fatty acids, linseed oil fatty acids and other drying oil and semi-drying oil fatty acids, $C_{8-18}$ OXO acids, and $C_{9-11}$ trialkylacetic acids.

Equivalent amounts of the metal and the organic monocarboxylic acid or a stoichiometric excess of either metal or acid may be used in this process. It is generally preferred that a 0.1% to 50% molar excess of the monocarboxylic acid be used.

In the process of this invention, the reaction of the polyvalent metal and organic monocarboxylic acid is carried out in the presence of an ammonium salt catalyst that is an ammonium salt of a mineral acid, an ammonium salt of a monocarboxylic acid having 1 to 4 carbon atoms, or a mixture of these ammonium salts. The ammonium salt catalyst is preferably a mixture that contains 10% to 90% by weight of at least one ammonium salt of a mineral acid, such as ammonium sulfate, ammonium nitrate, ammonium phosphate, ammonium chloride, ammonium fluoride, ammonium carbonate, and ammonium chlorate, and 10% to 90% by weight of at least one ammonium salt of an aliphatic monocarboxylic acid, such as ammonium formate, ammonium acetate, ammonium propionate, and ammonium butyrate. Particularly advantageous results have been obtained using a mixture that contained 30% to 70% by weight of an ammonium salt of a mineral acid and 30% to 70% by weight of an ammonium salt of a monocarboxylic acid. The amount of the ammonium salt catalyst that is used is that which will bring about the desired reduction in the time required for the polyvalent metal to react with the monocarboxylic acid to form the oil-soluble salt. It is dependent upon such factors as the choice of polyvalent metal, organic monocarboxylic acid, and ammonium salt catalyst and the reaction conditions employed. In most cases, the amount of the ammonium salt catalyst used is not more than 75% of the weight of metal in the reaction mixture.

The ammonium salt-catalyzed reaction between the polyvalent metal and organic monocarboxylic acid is carried out in the presence of water, oxygen, and an inert, water-immiscible organic solvent. The water does not take part in the reaction; it merely assists in distributing the catalyst uniformly throughout the reaction mixture. Water may be added to the reaction mixture before, during, or after the addition of the catalyst, or an aqueous solution of the catalyst may be added to the reaction mixture. The amount of water that is added is between about 20% and 80% of the weight of the metal, preferably between 40% and 60% of the weight of the metal.

Oxygen may be added to the reaction mixture as such or as a compound, for example, a peroxide, that will react under the reaction conditions to release oxygen. The addition of oxygen is usually accomplished by bubbling an oxygen-containing gas through the mixture during the reaction. The amount of oxygen that is added can be varied within wide limits. In most cases, air is bubbled through the reaction mixture at such a rate that a total of about 2 moles to 100 moles of oxygen is provided per mole of metal.

The preparation of the oil-soluble metal salts by the process of this invention is carried out in the presence of an inert, water-immiscible, organic solvent that is preferably an aliphatic or aromatic hydrocarbon or chlorinated hydrocarbon. Suitable solvents include such hydrocarbons as benzene, toluene, xylene, ethylbenzene, dipentene, turpentine, petroleum hydrocarbon fractions such as gasoline, mineral spirits, kerosene, mineral oil, fuel oil, and aromatic naphthas and such chlorinated hydrocarbons as carbon tetrachloride, o-dichlorobenzene, monochlorotoluene, ethylene dichloride, and perchloroethylene. If desired, mixtures of these solvents can be used.

This process for the production of oil-soluble polyvalent metal salts of organic monocarboxylic acids may be carried out under either atmospheric pressure or superatmospheric pressures. Although the rate of reaction is increased at superatmospheric pressures, it is usually more economical and more convenient to prepare the metal salts at atmospheric pressure. Reaction temperatures in the range of 70° C. to 150° C. may be used. Optimum results have been obtained when the reaction was carried out at a temperature in the range of 80° C. to 100° C.

The reaction between polyvalent metal and the organic monocarboxylic acid in the presence of an ammonium salt catalyst, water, an inert organic solvent, and oxygen is continued until substantially no unreacted metal remains in the reaction mixture or until the acid number of the reaction mixture has reached the desired level. When the reaction has been completed, the reaction mixture is heated to remove water from it and filtered to remove any insoluble materials that it contains. The product, which is a solution of a polyvalent metal salt of an organic monocarboxylic acid in an inert water-immiscible, organic solvent contains from about 3% to 36% by weight of the metal. It can be used without purification or treatment other than the adjustment of its metal content to the desired level in any of the applications in which these polyvalent metal salts are commonly used.

The invention is further illustrated by the following examples.

EXAMPLE 1

A. A mixture of 50 grams (0.852 mole) of powdered nickel (particle size 3 to 7 microns), 248 grams (1.710 moles) of 2-ethylhexanoic acid (acid number, 387), a catalyst solution prepared by dissolving 10 grams of ammonium nitrate and 5 grams of ammonium acetate in 30 grams of water, and 170 grams of mineral spirits was agitated and heated to 85° C. The reaction mixture was maintained at 80°-85° C. for 6 hours while it was sparged with air at the rate of 30 liters per hour. It was then heated to 135° C. under vacuum to remove water from it. After the reaction product had been filtered and diluted with mineral spirits, there was obtained a solution of nickel 2-ethylhexanoate in mineral spirits that contained 10% by weight of nickel and had an acid number of 21.7.

EXAMPLE 2

When the procedure described in Example 1 was repeated except that the catalyst was a solution of 15 grams of ammonium nitrate in 20 grams of water, a reaction period of 38 hours was required to produce the nickel 2-ethylhexanoate solution.

COMPARATIVE EXAMPLE A

When the procedure described in Example 1 was repeated except that an ammonium salt catalyst was not used, only slight reaction between the nickel and 2-ethylhexanoic acid occurred in a 20 hour heating period.

EXAMPLE 3

A mixture of 30 grams (0.509 mole) of powdered cobalt (100% through a 100 mesh screen), 298 grams (1.020 moles) of naphthenic acid (acid number, 192), a catalyst solution prepared by dissolving 10 grams of ammonium formate and 5 grams of ammonium sulfate in 27.5 grams of water, and 150 grams of mineral spirits was agitated and heated to 80° C. It was then sparged with air at the rate of 30 liters per hour while it was heated to 95° C. and maintained at that temperature for 7 hours. The reaction mixture was heated to 135° C. under vacuum to remove water from it, filtered, and diluted with mineral spirits. There was obtained a cobalt naphthenate solution in mineral spirits that contained 6% by weight of cobalt and had an acid number of 22.

COMPARATIVE EXAMPLE B

When the procedure described in Example 3 was repeated except that an ammonium salt catalyst was not used, a reaction period of 14 hours was required to produce the cobalt naphthenate solution.

EXAMPLE 4

A mixture of 46 grams (0.806 mole) of powdered iron (97.8% Fe) (100% through a 100 mesh screen), 292 grams (2.014 moles) of isooctanoic acid (acid number, 387), a catalyst solution prepared by dissolving 10 grams of ammonium fluoride and 5 grams of ammonium formate in 25 grams of water, and 170 grams of mineral spirits was sparged with air at the rate of 30 liters per hour until the exotherm had subsided. Sparging with air was continued while the reaction mixture was heated at 95° C. for 5 hours. It was then heated to 135° C. under vacuum to remove water from it, filtered, and diluted with mineral spirits. There was obtained a solution of iron isooctanoate in mineral spirits that contained 9.0% of iron.

COMPARATIVE EXAMPLE C

When the procedure described in Example 4 was repeated except that an ammonium salt catalyst was not used, a reaction period of 7 hours was required to produce the iron isooctanoate solution.

What is claimed is:

1. In the process for the production of oil-soluble metal salts wherein a reaction mixture that comprises a polyvalent metal, an organic monocarboxylic acid having 5 to 18 carbon atoms, water, and an inert, water-immiscible organic solvent is heated in the presence of oxygen for a period of time sufficient to form the metal salt of said monocarboxylic acid, the improvement wherein the reaction between the polyvalent metal and the monocarboxylic acid is carried out in the presence of an ammonium salt catalyst selected from the group consisting of ammonium salts of mineral acids, ammonium salts of organic monocarboxylic acids having 1 to 4 carbon atoms, and mixtures thereof.

2. The process of claim 1 wherein the ammonium salt catalyst is a mixture containing 10% to 90% by weight of an ammonium salt of a mineral acid and 10% to 90% by weight of an ammonium salt of a monocarboxylic acid having 1 to 4 carbon atoms.

3. The process of claim 2 wherein the ammonium salt catalyst is a mixture containing 30% to 70% by weight of an ammonium salt of a mineral acid and 30% to 70% by weight of an ammonium salt of a monocarboxylic acid having 1 to 4 carbon atoms.

4. The process of claim 1 wherein the ammonium salt catalyst comprises ammonium nitrate.

5. The process of claim 1 wherein the ammonium salt catalyst comprises an ammonium salt of a monocarboxylic acid having 1 to 4 carbon atoms.

6. The process of claim 1 wherein the ammonium salt catalyst is a mixture containing ammonium nitrate and an ammonium salt of a monocarboxylic acid having 1 to 4 carbon atoms.

7. The process of claim 1 wherein the amount of the ammonium salt catalyst used is not more than 75% of the weight of metal in the reaction mixture.

8. The process of claim 1 wherein the polyvalent metal is nickel.

9. The process of claim 1 wherein the polyvalent metal is cobalt.

10. The process of claim 1 wherein the polyvalent metal is iron.

* * * * *